United States Patent
Maibach et al.

(10) Patent No.: US 6,846,837 B2
(45) Date of Patent: Jan. 25, 2005

(54) TOPICAL ADMINISTRATION OF BASIC ANTIFUNGAL COMPOSITIONS TO TREAT FUNGAL INFECTIONS OF THE NAILS

(76) Inventors: Howard I. Maibach, 2745 Larkin St., San Francisco, CA (US) 94109; Eric C. Luo, 6833 Saint Lawrence St., Plano, TX (US) 75024; Tsung-Min Hsu, 11745 Stoney Peak Dr., Apt. #222, San Diego, CA (US) 92128

(*) Notice: Subject to any disclaimer, the term of this patent is extended or adjusted under 35 U.S.C. 154(b) by 0 days.

(21) Appl. No.: 10/178,074

(22) Filed: Jun. 21, 2002

(65) Prior Publication Data

US 2003/0235541 A1 Dec. 25, 2003

(51) Int. Cl.⁷ .................... A61K 33/00; A61K 33/02; A61K 33/08; A61K 31/137; A61K 31/4412
(52) U.S. Cl. .................. 514/350; 514/31; 514/159; 514/161; 514/162; 514/163; 514/164; 514/239.5; 514/252; 514/269; 514/274; 514/346; 514/383; 514/384; 514/396; 514/399; 514/400; 514/462; 514/557; 514/558; 514/560; 514/568; 514/588; 514/648; 514/649; 514/717; 514/738; 514/858; 514/937; 514/944; 514/946; 514/947; 514/964; 514/969; 424/411; 424/445; 424/447; 424/448; 424/449; 424/484; 424/670; 424/682; 424/688; 424/690; 424/692; 424/693; 424/719; 424/722
(58) Field of Search .................. 514/31, 159, 161–164, 514/239.5, 252, 269, 274, 346, 350, 383, 384, 396, 399, 400, 462, 557, 558, 560, 568, 588, 648, 649, 717, 738, 858, 937, 944, 946, 947, 964, 969; 424/411, 445, 447, 448, 449, 484, 670, 682, 688, 690, 692, 693, 719, 722

(56) References Cited

U.S. PATENT DOCUMENTS

| | | |
|---|---|---|
| 4,172,888 A | 10/1979 | Delzell, Sr. |
| 4,810,496 A * | 3/1989 | Jensen .................. 424/646 |
| 5,661,170 A | 8/1997 | Chodosh |
| 5,681,853 A | 10/1997 | Yu et al. |
| 5,696,164 A | 12/1997 | Sun et al. |
| 5,827,870 A | 10/1998 | Chodosh |
| 5,834,510 A | 11/1998 | Yu et al. |
| 5,883,128 A | 3/1999 | Yu et al. |
| 5,886,041 A | 3/1999 | Yu et al. |
| 5,886,042 A | 3/1999 | Yu et al. |
| 5,942,250 A | 8/1999 | Yu et al. |
| 5,968,986 A | 10/1999 | Dyer |
| 5,993,790 A | 11/1999 | Strauss |
| 5,994,383 A | 11/1999 | Dyer et al. |
| 5,994,403 A | 11/1999 | Donatiello |
| 6,013,677 A | 1/2000 | Dyer |
| 6,022,549 A | 2/2000 | Dyer |
| 6,087,400 A | 7/2000 | Dyer |
| 6,143,794 A | 11/2000 | Chaudhuri et al. |
| 6,166,078 A | 12/2000 | Cantin et al. |
| 6,586,000 B2 * | 7/2003 | Luo et al. .................. 424/449 |

FOREIGN PATENT DOCUMENTS

| | | |
|---|---|---|
| WO | WO 01/15670 | 3/2001 |
| WO | WO 01/43775 | 6/2001 |
| WO | WO 02/15936 | 2/2002 |

OTHER PUBLICATIONS

U.S. Appl. No. 10/177,436, filed Jun. 20, 2002, Hsu et al.
Brodell et al. (1991), "Office Dermatologic Testing: The KOH Preparation," *Am. Fam. Phys.* 43(6):2061–2065.
Chang et al. (1994), "Onychomycosis in Children," *International Journal of Dermatology* 33(8):550–551.
Elewski (1996), "Diagnostic Techniques for Confirming Onychomycosis," *Journal of the American Academy of Dermatology* 35(3, Part 2):S6–S9.
Hicks (1977), "Erythema Nodosum in Patients with Tinea Pedis and Onychomycosis," *Southern Medical Journal* 70(1):27–28.
Mehregan et al. (1997), "Onychomycosis," *Cutis* 59(5):247–248.
Milles e tal. (1998), "Onychomycosis: Diagnosis and Systemic Treatment," *The Nurse Practitioner* 23(12):40–51.
Zaias et al. (1996), "Diagnosing and Treating Onychomycosis," *The Journal of Family Practice* 42(5):513–518.

* cited by examiner

Primary Examiner—John Pak
(74) Attorney, Agent, or Firm—Reed Intellectual Property Law Group

(57) ABSTRACT

Methods and topical pharmaceutical formulations are provided for the treatment of nail fungus (onychomycosis). The invention involves a pharmacologically active antifungal agent, plus a pharmaceutically acceptable base in a formulation having a pH of 7.5 to about 13.0, preferably about 8.0 to 11.5, and most preferably about 8.5 to 10.5. These basic formulations permeate the nail and are effective in treating fungal infections of the nail and surrounding tissues.

32 Claims, No Drawings

TOPICAL ADMINISTRATION OF BASIC ANTIFUNGAL COMPOSITIONS TO TREAT FUNGAL INFECTIONS OF THE NAILS

TECHNICAL FIELD

This invention relates generally to methods and pharmaceutical formulations for treating fungal infections of the nail and adjacent tissue. More particularly, this invention relates to the use of a pharmacologically active base in such methods and formulations.

BACKGROUND

Introduction

Fungal infections of the nail, referred to by the terms "nail fungus," "onychomycosis," or "tinea unguium," are common throughout the world. An estimated 2–13% of the population is affected in North America, with at least 15–20% of those aged 40–60 having one or more fingernails or toenails infected. Toenails are much more commonly affected than fingernails. Infections can range from superficial, causing little more than discoloration, to severe, resulting in loss of the nail together with deformities of the surrounding digit. The incidence of onychomycosis has been rising over the past few decades, due to factors such as an increased elderly population, increased participation in vigorous physical activity while wearing moisture-retaining shoes and socks, an increase in the number of HIV infected individuals, an increased incidence of diabetes, and increased use of steroids, antibiotics, and other therapeutics that can suppress immunologic responses to fungi.

While nail fungus is rarely life threatening, it causes significant pain, inconvenience, embarrassment, emotional distress, and limitations to manual performance and ambulation. Individuals with moderate to severe onychomycosis can lose their ability to perform many routine tasks (such as fastening buttons, picking up small objects, walking significant distances) and can lose the ability to perform satisfactorily in their occupations. Due to the unpleasant appearance of their hands or feet, these individuals may become socially self-conscious and embarrassed, and may avoid intimate or other close contact with people. Loss of self-esteem, anxiety, and depression commonly result from moderate to severe cases of fungal nail infection.

At present, topical treatments for nail fungus are rarely effective. Although some oral antifungal therapies have moderate efficacy, they also pose significant risks of toxic reactions, and many patients would prefer local, topical treatments to systemic treatments.

Etiology and Varieties

Onychomycosis is caused most commonly by several species of dermatophytes (parasitic fungi that infect the keratin-rich tissue of the stratum corneum, hair, and nails) and, less commonly, by nondermatophyte molds or by yeasts, primarily of the genus *Candida*. An estimated 90% of cases are caused by dermatophytes, primarily of the genera *Trichophyton, Microsporum*, and *Epidermophyton*, while about 8% are caused by nondermatophyte molds and 2% by yeasts. The causative agent in onychomycosis can rarely be determined by clinical appearance; microscopic examination or culturing is usually required. Furthermore, an infected nail colonized by one species can develop secondary infections by other fungi, yeasts, or bacteria.

Onychomycosis can affect the nail plate, the nail bed (the tissue directly under the nail plate), the nail matrix or nail root (the thickened skin at the base of the nail from which the nail plate develops), the cuticle, the hyponychium (the thickened layer of epidermis beneath the free end of the nail), and the proximal and lateral nail folds (the skin adjacent to the base and sides of the nail).

Factors that contribute to the development of onychomycosis include advanced age, diabetes (which reduces circulation to the extremities), wearing heat- and moisture-retaining footwear, communal bathing, HIV infection, the use of antibiotics or immunosuppressive drugs, trauma to the nail, use of insufficiently cleaned manicure tools, poor overall health, and warm climates.

Onychomycosis can be categorized into several varieties based on clinical appearance. The recognized varieties include:

Distal and lateral subungual onychomycosis (DLSO): This is the most common variety. It usually results from a fungal infection of the skin (usually the plantar skin of the foot) spreading to the nail bed and then to the underside of the nail plate via the hyponychium. The distal and lateral parts of the nail plate become thickened, white, and opaque. In addition, the nail bed becomes hyperkeratotic and onycholysis (separation of the nail plate from the bed, ultimately resulting in loss of the nail) commonly ensues. Paronychia (inflammation of the tissues adjacent to the nail) is also common. *Trichophyton rubrum* is the most common pathogen.

Endonyx onychomycosis (EO): This is a variety of DLSO in which the fungus spreads directly from the skin to the nail plate rather than to the nail bed. The nail again is thickened, white, and opaque, but there is no evident nail bed hyperkeratosis or onycholysis.

White superficial onychomycosis (WSO): This variety is almost always found on toenails. The surface of an infected nail develops white dots or powdery patches and the nail becomes rough and crumbly. *Trichophyton mentagrophytes* (*T. interdigitale*) is the most common cause, though some nondermatophyte molds such as *Acremonium, Aspergillus*, and *Fusarium* can also infect the upper surface of the nail plate. The nondermatophyte molds commonly cause black or green nails.

Proximal subungual onychomycosis (PSO): In this least common variety, the fungus first attacks the cuticle and proximal nail fold, and then penetrates the proximal nail plate. The distal part of the nail remains normal.

*Candida* Onychomycosis (CO): The yeast, nearly always *Candida albicans*, infects the nail folds (paronychia), the nail plate and surrounding tissues (in chronic mucocutaneous candidiasis), the nail bed, or any combination of these. The entire digit commonly becomes swollen and deformed. *Candida* may cause onycholysis or it may colonize onycholytic nails (resulting from trauma or another infection). *Candida* infection associated with paronychia is almost always secondary to trauma to the nail folds.

Total dystrophic onychomycosis (TDO): The entire nail plate is thickened, yellow-brown, and opaque. All the adjacent tissues are affected, and the nail matrix may be permanently damaged, preventing normal nail growth even after the infection resolves. TDO can be the endpoint of any of the other onychomycosis varieties.

A patient with onychomycosis may have one variety or any combination of varieties.

Current Treatments

Onychomycosis is presently treated primarily with oral antifungal agents. Topical agents are rarely effective by themselves, except in mild cases that only affect the distal nail plate. They may, however, be beneficial in combination with oral therapy. In severe cases, the affected nail (and sometimes the nail bed and matrix) is removed surgically or by use of a urea containing formulation; removal of the nail is done in conjunction with oral and sometimes topical therapy. Further details on some of these methods follow.

Oral medications: The preferred therapy for onychomycosis is orally administered treatment with terbinafine (Lamisil™), itraconazole (Sporanox™), or fluconazole (Diflucan™). Terbinafine, an allylamine, is active against dermatophytes, but has considerably less efficacy against nondermatophyte molds and against yeasts. Itraconazole and fluconazole are triazoles that are effective against dermatophytes, nondermatophyte molds, and yeasts. When administered daily, all of these compounds can cause hepatic injury, and monitoring of liver enzymes is required. Pulse therapy (typically, administration one week per month) reduces the risks for hepatic damage, but prolongs the course of therapy from about 6 to 12 weeks to at least several months. Terbinafine has several potentially serious drug interactions, and the triazoles, because they are metabolized using the hepatic cytochrome P450 system, have numerous significant drug and food interactions that prevent their use in many patients. Even though these drugs are the currently preferred treatments for onychomycosis, their cure rates are not high: a recent survey (Arch Dermatol 134(12):1551–1554, 1998) found that standard treatment with terbinafine resulted in disease-free nails in approximately 35–50% of cases, while the rate for itraconazole was approximately 25–40%. Relapse is also common, though precise figures are not available. These oral therapies are nevertheless more effective than topical treatments because they apparently penetrate the nail more quickly and thoroughly, and because they remain in the nail for weeks or months following treatment.

Topical treatments: Topical antifungal treatments are now administered mainly in cases where the fungal infection is restricted to the distal half of the nail plate or in cases in which the patient cannot tolerate oral therapy. Again, their low efficacies appear due mainly to their inability to adequately penetrate the nail. Topical antifungal agents include allylamines (including terbinafine), triazoles (including itraconazole and fluconazole), imidazole derivatives (including ketoconazole, miconazole, clotrimazole, and enconazole), amorolfine, ciclopirox olamine, sodium pyrithione, bifonazole plus urea, and propylene glycol plus urea plus lactic acid.

Existing treatments for onychomycosis are thus of limited efficacy, have high risks for adverse effects and drug interactions, and are time consuming and inconvenient for the patient. Furthermore, (based on conversations with practicing dermatologists) a large majority of onychomycosis patients would prefer a local, topical treatment to a systemic treatment that carries a significant risk of adverse effects. It has now been discovered that certain basic compositions, when used as described herein to enhance the permeation of antifungal compounds into the nail and surrounding tissues, successfully treat nail fungus locally, with much higher efficacy than for other topical treatments. The present invention provides a novel treatment for nail fungus that is effective, safe, not painful, and convenient.

SUMMARY OF THE INVENTION

It is accordingly a primary object of the invention to address the above needs in the art by providing a novel method and formulation for the treatment of fungal infections of the nail and surrounding tissues (onychomycosis).

The invention provides a method and formulation for the treatment of onychomycosis that involves a topically applied formulation containing a pharmacologically active base in an amount effective to provide the formulation with a pH in the range of about 7.5 to 13.0, preferably about 8.0 to 11.5, and most preferably about 8.5 to 10.5. The base itself has antifungal activity, but additional antifungal agents may be incorporated into the formulation as well, in which case the base not only provides antifungal activity but also enhances the permeation of the additional antifungal agent(s) into and through the skin. The formulation may be a lotion, cream, solution, paste, ointment, plaster, paint, bioadhesive, or the like, or may be contained in a tape or in a skin patch comprised of a laminated composite intended for long-term adhesion to the body surface (typically throughout a delivery period in the range of about 8 to about 72 hours) in the affected area.

DETAILED DESCRIPTION OF THE INVENTION

I. Definitions and Nomenclature

Before describing the present invention in detail, it is to be understood that this invention is not limited to specific pharmacologically active bases, antifungal agents, carriers, formulation types, treatment regimens, and so forth, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise.

The term "onychomycosis" is used herein to refer to any fungal infection of the fingernail or toenail; such infection commonly encompasses some or all of the surrounding tissues. Surrounding tissues comprise the nail bed, the nail matrix, the nail root, the nail folds, the cuticle, and the hyponychium. Infection may be by dermatophytes, nondermatophyte molds, yeasts, other fungi, or combinations of these. Infecting dermatophytes include, without limitation, members of the genera *Trichophyton* (including *T. rubrum, T. interdigitale* (*T. mentagrophytes*), and *T. soudanense*), *Epidermophyton,* and *Microsporum.* Infecting nondermatophyte molds include, without limitation, members of the genera *Acremonium, Aspergillus, Fusarium, Onychocola,* and *Scytalidium.* Infecting yeasts include, without limitation, members of the genus *Candida,* including *Candida albicans.* The terms "onychomycosis", "tinea unguium", "nail fungus", and "fungal infection of the nail" all have essentially the identical meaning and are used interchangeably herein.

The term "pharmacologically active base" is used herein to refer to a basic compound or composition of matter that is an effective antifungal agent and that, when included in a topical pharmaceutical formulation that contains one or more additional pharmacologically active antifungal agents, enhances permeation of the formulation and the additional antifungal agent(s) into the nail or skin of a human patient. The term "enhances permeation" is used herein to refer to an increase in permeation by the pharmacologically active antifungal agent into the nail or skin of at least 20%, preferably at least 50%, and more preferably at least 100%.

The terms "pharmacologically active antifungal agent" and "antifungal agent" are used herein interchangeably to refer to a pharmaceutically acceptable agent that, when topically administered to a human patient together with a pharmacologically active base of the invention, induces a desired pharmacologic and/or physiologic effect by local and/or systemic action, i.e., prevention or treatment of onychomycosis. Also included are derivatives and analogs of those compounds or classes of compounds specifically mentioned that also induce the desired effect.

By "pharmaceutically acceptable," such as in the recitation of a "pharmaceutically acceptable carrier," or a "pharmaceutically acceptable derivative," is meant a compound that is not biologically or otherwise undesirable, i.e., the compound may be incorporated into a topical formulation of the invention and administered to a patient without causing any undesirable biological effects or interacting in a deleterious manner with any of the other components of the formulation in which it is contained. A "pharmacologically active" compound refers to an active agent as defined above, or to an analog or derivative thereof having the same type of pharmacological activity as the parent compound.

The terms "treating" and "treatment" as used herein refer to actions that reduce the severity and/or frequency of symptoms, eliminate symptoms and/or their underlying cause, prevent the occurrence of symptoms and/or their underlying cause, and improve or remediate damage. The present method of "treating" a patient, as the term is used herein, thus encompasses both prevention of onychomycosis in a predisposed individual and treatment of onychomycosis in a clinically symptomatic individual.

The term "base" is used in its traditional sense, i.e., a substance that dissolves in water to produce hydroxide ions. The water is typically an aqueous fluid, and may be natural moisture at the skin surface, or the patch or composition that is used may contain added water, and/or be used in connection with an occlusive backing. Similarly, any liquid or semisolid formulation that is used is preferably aqueous or used in conjunction with an overlayer of an occlusive material. Any base may be used provided that the compound provides free hydroxide ions in the presence of an aqueous fluid. Bases can provide free hydroxide ions either directly or indirectly and thus can also be referred to as "hydroxide-releasing agents". Hydroxide-releasing agents that provide free hydroxide ions directly, typically contain hydroxide groups and release the hydroxide ions directly into solution, for example, alkali metal hydroxides. Hydroxide-releasing agents that provide free hydroxide ions indirectly, are typically those compounds that are acted upon chemically in an aqueous environment and the reaction produces hydroxide ions, for example metal carbonates or amines.

By an "effective" amount or a "therapeutically effective amount" of a pharmacologically active agent is meant a nontoxic but sufficient amount of the drug or agent to provide the desired effect, i.e., prevention or treatment of onychomycosis. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term "topical administration" is used in its conventional sense to mean delivery of a topical drug or pharmacologically active agent to the skin, nail, or mucosal tissue, as in, for example, the treatment of onychomycosis.

The term "body surface" is used to refer to skin, nail, or mucosal tissue.

"Carriers" or "vehicles" as used herein refer to pharmaceutically acceptable carrier materials suitable for topical drug administration. Carriers and vehicles useful herein include any such materials known in the art that are nontoxic and do not interact with other components of the composition in a deleterious manner.

The term "aqueous" refers to a formulation that contains water or that becomes water-containing following application to the skin, nail, or mucosal tissue.

In describing molecular structures and formulae herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" denotes an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" denotes an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring and are referred to as "monocyclic aryls." "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "heteroatom-containing" as in a "heteroatom-containing hydrocarbyl group" refers to a molecule or molecular fragment in which one or more carbon atoms are replaced with an atom other than carbon, e.g., nitrogen, oxygen, sulfur, phosphorus, or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl, and alkynyl" is to be interpreted as "heteroatom-containing alkyl, heteroatom-containing alkenyl, and heteroatom-containing alkynyl."

By "substituted", as in "substituted alkyl," "substituted alkenyl," "substituted aryl," and the like, as alluded to in some of the aforementioned definitions, is meant that in the alkyl, alkenyl, aryl, or other moiety, at least one hydrogen atom bound to a carbon atom is replaced with one or more substituents that are functional groups such as hydroxyl, alkoxy, thio, amino, halo, and the like.

The terms "alkyl," "alkenyl," "aryl," and the like are, unless otherwise indicated, intended to include unsubstituted, substituted, heteroatom-containing, and substituted heteroatom-containing substituents.

II. Indications

The invention pertains to treatment of an individual predisposed to or afflicted with onychomycosis, comprising topically administering a pharmaceutical formulation containing a base to the affected skin area, wherein the formulation preferably has a pH in the range of about 7.5 to about 13.0, preferably about 8.0 to 11.5, more preferably about 8.5 to 11.5, and most preferably about 8.5 to 10.5. In some aspects, the pH will be in the range of about 9.5 to 11.5, preferably 10.0 to about 11.5. The formulation will generally include a pharmacologically active antifungal agent as well, in which case the base serves as a permeation enhancer for the agent. Inclusion of the antifungal agent is optional, however, insofar as the base does exhibit some antifungal activity. The term "onychomycosis" comprises any fungal infection of the fingernail or toenail and surrounding tissues, including infection by dermatophytes, nondermatophyte molds, and yeasts.

III. The Pharmacologically Active Base

The pharmacologically active base of the invention is an inorganic or an organic pharmaceutically acceptable base. Preferred inorganic bases include inorganic hydroxides, inorganic oxides, inorganic salts of weak acids, and combinations thereof. Preferred organic bases are nitrogenous bases.

It has long been thought that strong bases, such as NaOH, were not suitable for administration to skin because they would damage skin. It has been now been discovered that the skin permeability of various drugs could be enhanced without skin damage by exposing the skin to a base or basic solution, in a skin contacting formulation or patch. The desired pH of the solution on the skin can be obtained using a variety of bases or base concentrations. Accordingly, the pH is selected so as to be low enough so as to not cause skin damage, but high enough to enhance skin permeation to various active agents. As such, it is important that the amount of base in any patch or formulation is optimized so as to increase the flux of the drug through the body surface while minimizing any possibility of skin damage. In general, this means that the pH at the body surface in contact with a formulation or drug delivery system of the invention is preferably in the range of approximately 8.0 to 13.0, preferably about 8.0 to 11.5, more preferably about 8.5 to 11.5 and most preferably about 8.5 to 10.5. In some aspects, the pH will be in the range of about 9.5 to 11.5, preferably 10.0 to about 11.5.

In one preferred embodiment, the pH at the body surface is the primary design consideration, i.e., the composition or system is designed so as to provide the desired pH at the body surface. Anhydrous formulations and transdermal systems may not have a measurable pH, and the formulation or system can be designed so as to provide a target pH at the body surface. Moisture from the body surface can migrate into the formulation or system, dissolve the base and thus release the base into solution, which will then provide the desired target pH at the skin's surface. In those instances, a hydrophilic composition is preferred. In addition, when using aqueous formulations, the pH of the formulation may change over time after it is applied on the skin. For example, gels, solutions, ointments, etc., may experience a net loss of moisture after being applied to the body surface, i.e., the amount of water lost is greater than the amount of water received from the body surface. In that case, the pH of the formulation may be different than its pH when manufactured. This problem can be easily remedied by designing the aqueous formulations to provide a target pH at the skin's surface.

In other embodiments of the invention, the pH of the formulation or the drug composition contained within a delivery system will be in the range of approximately 8.0 to 13.0, preferably about 8.0 to 11.5, most preferably about 8.5 to 11.5, and most preferably about 8.5 to 10.5. In some aspects, the pH will be in the range of about 9.5 to 11.5, preferably 10.0 to 11.5. In one embodiment of the invention the pH of the formulation is higher than the pH at the body surface. For example, if an aqueous formulation is used, moisture from the body surface can dilute the formulation, and thus provide for a different pH at the body surface, which will typically be lower than that of the formulation itself.

In one preferred embodiment, the body surface is exposed to a base or basic solution for a sufficient period of time so as to provide a high pH at the body surface, thus creating channels in the skin or mucosa for the drug to go through. It is expected that drug flux is proportional to the strength of the solution and the duration of exposure. However, it is desirable to balance the maximization of drug flux with the minimization of skin damage. This can be done in numerous ways. For example, the skin damage may be minimized by selecting a lower pH within the 8.0 to 13.0 range, by exposing the skin to the formulation or system for a shorter period of time, or by including at least one irritation-mitigating additive. Alternatively, the patient can be advised to change the location of application with each subsequent administration.

While certain preferred amounts are set forth below, it is understood that, for all of the inorganic and organic bases described herein, the optimum amount of any such base will depend on the strength or weakness of the base and its molecular weight, and other factors such as the number of ionizable sites in the active agent being administered and whether there are any acidic species present in the formulation or patch. One skilled in the art may readily determine the optimum amount for any particular base such that the degree of enhancement is optimized while the possibility of damage to the body surface is eliminated or at least substantially minimized.

Inorganic Base

Exemplary inorganic bases are inorganic hydroxides, inorganic oxides, inorganic salts of weak acids, and combinations thereof. Preferred inorganic bases are those whose aqueous solutions have a high pH, and are acceptable as food or pharmaceutical additives. Examples of such preferred inorganic bases are those listed below, along with their respective pHs. Some of the bases are identified by their hydrate forms, and it is understood that when referring to a "base", both the hydrated and non-hydrated forms are intended to be included.

| Inorganic base | pH of Aqueous Solution (concentration) |
| --- | --- |
| Ammonium hydroxide[1,2,3] | 11.27 (1 N), 10.27 (0.001 N) |
| Sodium hydroxide[1,2,3] | 14(5%), 13 (0.5%), 12 (0.05%) |
| Potassium hydroxide[1,2,3] | 13.5 (0.1 M) |
| Calcium hydroxide[1,3] | 12.4 (saturated solution in water) |

-continued

| Inorganic base | pH of Aqueous Solution (concentration) |
| --- | --- |
| Magnesium hydroxide[1,3] | 9.5 to 10.5 slurry |
| Magnesium oxide[1,2,3] | 10.3 (saturated aqueous solution) |
| Calcium oxide[3] | Soluble in water, Form Ca(OH)$_2$ |
| Sodium acetate[1,3] | ~8.9 (0.1 N) |
| Sodium acetate, trihydrate[1,2] | 8.9 (0.1 N) |
| Sodium acetate, anhydrous[1,2] | ~8.9 (0.1 N) |
| Sodium borate decahydrate[1,2] | ~8.8–9.4, 9.15 to 9.2 (0.01 M) |
| Sodium borate[1,2,3] | 8.8–9.4, 9.15 to 9.2 (0.01 M) |
| Sodium metaborate | Strongly alkaline |
| Sodium carbonate[1,2,3] | ~11.6 |
| Sodium carbonate hydrate[1] | ~11.6 |
| Sodium carbonate anhydrous | ~11.6 |
| Sodium bicarbonate[1,2,3] | 8.3 (0.1 M fresh) |
| Sodium phosphate, tribasic[1,3] | ~11.5 (0.1%), ~11.7 (0.5%), ~11.9 (1.0%) |
| Sodium phosphate, tribasic dodecahydrate | 11.5 (0.1%), 11.7 (0.5%), 11.9 (1.0%) |
| Sodium phosphate, dibasic, anhydrous[1,2] | 9.1 (1%) |
| Sodium phosphate, dibasic, heptahydrate[1,2] | ~9.5 |
| Sodium phosphate, dibasic[1,3] | ~9.5 |
| Sodium phosphate, dibasic, dihydrate[1] | ~9.5 |
| Sodium phosphate, dibasic, dodecahydrate | ~9.5 |
| Potassium carbonate[1,3] | ~11.6 |
| Potassium bicarbonate[3] | 8.2 (0.1 M) |
| Potassium citrate[1,2,3] | ~8.5 |
| Potassium citrate monohydrate | ~8.5 |
| Potassium acetate[1,3] | 9.7 (0.1 M) |
| Potassium phosphate, dibasic[1,2] | Aqueous solution is slightly alkaline |
| Potassium phosphate, tribasic[3] | Aqueous solution is strongly alkaline |
| Ammonium phosphate, dibasic[1,2,3] | ~8 |

[1] listed in the "Chemicals in Compliance with Pharmaceutical Standards: Inactive Ingredient Guide"
[2] listed in the "Handbook of Pharmaceutical Additives"
[3] listed in the FDA's food additive database Inorganic Hydroxides Inorganic hydroxides include, for example, ammonium hydroxide, alkali metal hydroxide and alkaline earth metal hydroxides, and mixtures thereof. Preferred inorganic hydroxides include ammonium hydroxide; monovalent alkali metal hydroxides such as sodium hydroxide and potassium hydroxide; divalent alkali earth metal hydroxides such as calcium hydroxide and magnesium hydroxide; and combinations thereof.

The amount of inorganic hydroxide included in the compositions and systems of the invention, will typically represent about 0.3–7.0 wt %, preferably 0.5–4.0 wt %, more preferably about 0.5–3.0 wt %, most preferably about 0.75–2.0 wt %, of a topically applied formulation or of a drug reservoir of a drug delivery system, or patch.

The aforementioned amounts are particularly applicable to those formulations and patches in which the active agent is (1) an uncharged molecule, e.g., wherein a basic drug is in nonionized, free-base form, (2) a basic salt of an acidic drug, or (3) there are no additional species in the formulation or patch that could react with or be neutralized by the inorganic hydroxide, to any significant degree.

For formulations and patches in which the drug is in the form of an acid addition salt, and/or wherein there are additional species in the formulations or systems that can be neutralized by or react with the inorganic base (i.e., acidic inactive ingredients), the amount of inorganic hydroxide is preferably the total of (1) the amount necessary to neutralize the acid addition salt and/or other base-neutralizable species (i.e., the "acidic species"), plus (2) about 0.3–7.0 wt %, preferably 0.5–4.0 wt %, more preferably about 0.5–3.0 wt %, most preferably about 0.75–2.0 wt %, of the formulation or drug reservoir. That is, for an acid addition salt, the enhancer is preferably present in an amount just sufficient to neutralize the salt, plus an additional amount (i.e., about 0.3–7.0 wt %, preferably 0.5–4.0 wt %, more preferably about 0.5–3.0 wt %, most preferably about 0.75–2.0 wt %) to enhance the flux of the drug through the skin or mucosal tissue. Basic drugs in the form of a neutral, free base or basic salt of acidic drug are usually not affected by a base, and thus for these drugs, the amount in (1) is usually the amount necessary to neutralize inactive components that are acidic. For patches, the aforementioned percentages are given relative to the total weight of the formulation components and the adhesive, gel or liquid reservoir.

Still greater amounts of inorganic hydroxide may be used by controlling the rate and/or quantity of release of the base, preferably during the drug delivery period itself.

Inorganic Oxides

Inorganic oxides include, for example, magnesium oxide, calcium oxide, and the like.

The amount of inorganic oxide included in the compositions and systems of the invention may be substantially higher than the numbers set forth above for the inorganic hydroxide, and may be as high as 20 wt %, in some cases as high as 25 wt % or higher, but will generally be in the range of about 2–20 wt %. These amounts may be adjusted to take into consideration the presence of any base-neutralizable species.

Inorganic Salts of Weak Acids

Inorganic salts of weak acids include, ammonium phosphate (dibasic); alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic); alkaline earth metal salts of weak acids such as magnesium phosphate and calcium phosphate; and the like, and combinations thereof.

Preferred inorganic salts of weak acids include, ammonium phosphate (dibasic) and alkali metal salts of weak acids.

The amount of inorganic salts of weak acids included in the compositions and systems of the invention may be substantially higher than the numbers set forth above for the inorganic hydroxide, and may be as high as 20 wt %, in some cases as high as 25 wt % or higher, but will generally be in the range of approximately 2–20 wt %. These amounts may be adjusted to take into consideration the presence of any base-neutralizable species.

Organic Bases

Organic bases suitable for use in the invention are compounds having an amino group, amido group, an oxime, a cyano group, an aromatic or non-aromatic nitrogen-containing heterocycle, a urea group, and combinations thereof. More specifically, examples of suitable organic bases are nitrogenous bases, which include, but are not limited to, primary amines, secondary amines, tertiary amines, amides, oximes, cyano (—CN) containing groups, aromatic and non-aromatic nitrogen-containing heterocycles, urea, and mixtures thereof. Preferred organic bases are primary amines, secondary amines, tertiary amines, aromatic and non-aromatic nitrogen-containing heterocycles, and mixtures thereof.

For nitrogenous bases, the amount of the agent will typically represent about 0.5–4.0 wt %, preferably about 0.5–3.0 wt %, more preferably about 0.75–2.0 wt %, of a topically applied formulation or of a drug reservoir of a drug delivery system or a patch. These amounts may be adjusted to take into consideration the presence of any base-neutralizable species.

Still greater amounts of the nitrogenous base may be used depending on the strength of the base and the rate and/or quantity of release of the nitrogenous base preferably during the drug delivery period itself.

Preferred organic bases are those whose aqueous solutions have a high pH or a high pKa (more preferably a pKa>9), and are acceptable as food or pharmaceutical additives. Examples of such preferred organic bases are those listed below, along with their respective pHs (or pKa values).

| Organic base | pH of Aqueous Solution (concentration) |
|---|---|
| 2-amino-2-methyl-1,3-propanediol[1] | 10.8 (0.1 m) |
| 2-amino-2-methyl-1-propanol[1] | 11.3 (0.1 m) |
| Diethanolamine[1] | 11.0 (0.1 N) |
| Triethanolamine[1] | 10.5 (0.1 N) |
| Butylamine[2] | pKa = 10.56 |
| Dimethylamine[2] | Strong base, pKa = 10.73 |
| Cyclohexylamine[2] | Strong base, pKa = 10.64 |
| Ethylenediamine[2] | Strong base, pKa = 10.71 |
| Isopentylamine[2] | pKa = 10.6 |
| Monoethanolamine[2] | 12.1 (25%), 12.05 (0.1 N), pKa = 9.4 |
| Phenethylamine[2] | Strong base, pKa = 9.83 |
| Piperidine[2] | Strong base, pKa = 11.12 |
| Pyrrolidine[2] | Strong base, pKa = 11.27 |
| Trimethylamine[2] | Strong base, pKa = 9.81 |

[1]listed in the "Handbook of Pharmaceutical Additives"
[2]listed in the FDA's food additive database

Amines

Suitable nitrogenous bases may contain any one or a combination of the following:

primary amino (—NH$_2$) groups;

mono-substituted (secondary) amino groups —NHR where R is hydrocarbyl, generally either alkyl or aryl, e.g., lower alkyl or phenyl, and may be substituted with one or more nonhydrocarbyl substituents, e.g., 1 to 3 halo, hydroxyl, thiol, or lower alkoxy groups (such —NHR groups include, for example, methylamino, ethylamino, isopropylamino, butylamino, cyclopropylamino, cyclohexylamino, n-hexylamino, phenylamino, benzylamino, chloroethylamino, hydroxyethylamino, etc.);

di-substituted (tertiary) amino groups —NR$^a$R$^b$ where R$^a$ and R$^b$ may be the same or different and are as defined above for R (suitable —NR$^a$R$^b$ include, for example, dimethylamino, diethylamino, diisopropylamino, dibutylamino, methylpropylamino, methylhexylamino, methylcyclohexylamino, ethylcyclopropylamino, ethylchloroethylamino, methylbenzylamino, methylphenylamino, methyltoluylamino, methyl-p-chlorophenylamino, methylcyclohexylamino, etc.);

amides —(CO)—NR$^c$R$^d$ where R$^c$ and R$^d$ may be the same or different and are either hydrogen or R, wherein R is as defined above (including, for example, amides wherein one of R$^c$ and R$^d$ is H and the other is methyl, butyl, benzyl, etc.);

cyano (—CN);

aromatic nitrogen-containing heterocycles, typically five- or six-membered monocyclic substituents, or bicyclic fused or linked five- or six-membered rings (such as pyrrolyl, pyrrolidinyl, pyridinyl, quinolinyl, indolyl, pyrimidinyl, imidazolyl, 1,2,4-triazolyl, tetrazolyl, etc.); and non-aromatic nitrogen-containing heterocycles, typically four- to six-membered rings, including lactams and imides, e.g., pyrrolidino, morpholino, piperazino, piperidino, N-phenyl—propiolactam, -butyrolactam, -caprolactam, acetimide, phthalimide, succinimide, etc.

Primary amines, secondary amines, and tertiary amines may be generically grouped as encompassed by the molecular structure NR$^1$R$^2$R$^3$ wherein R$^1$, R$^2$ and R$^3$ are selected from H, alkyl, hydroxyalkyl, alkoxyalkyl, alkenyl, hydroxyalkenyl, alkoxyalkenyl, cycloalkyl, cycloalkyl-substituted alkyl, monocyclic aryl, and monocyclic aryl-substituted alkyl, with the proviso that at least one of R$^1$, R$^2$ and R$^3$ is other than H. Examples of such amines include, without limitation, diethanolamine, triethanolamine, isopropanolamine, triisopropanolamine, dibutanol amine, tributanol amine, N-dodecylethanolamine, N-(2-methoxyethyl) dodecylamine, N-(2,2-dimethoxyethyl) dodecylamine, N-ethyl-N-(dodecyl)ethanolamine, N-ethyl-N-(2-methoxyethyl)dodecylamine, N-ethyl-N-(2,2-dimethoxyethyl) dodecylamine, dimethyldodecylamine-N-oxide, monolauroyl lysine, dipalmitoyl lysine, dodecylamine, stearylamine, phenylethylamine, triethylamine, PEG-2 oleamine, PEG-5 oleamine, dodecyl 2-(N,N-dimethylamino)propionate, bis(2-hydroxyethyl) oleylamine, and combinations thereof.

Exemplary primary amines include 2-aminoethanol, 2-aminoheptane, 2-amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, methylamine, α-methylbenzylamine, phenethylamine, propylamine, and tris(hydroxymethyl)aminomethane.

Exemplary secondary amines include compounds that contain groups such as methylamino, ethylamino, isopropylamino, butylamino, cyclopropylamino, cyclohexylamino, n-hexylamino, phenylamino, benzylamino, chloroethylamino, hydroxyethylamino, and so forth. Exemplary secondary amines include diethanolamine, diethylamine, diisopropylamine, and dimethylamine.

Exemplary tertiary amines include compounds that contain groups such as dibutylamino, diethylamino, dimethylamino, diisopropylamino, ethylchloroethylamino, ethylcyclopropylamino, methylhexylamino, methylcyclohexylamino, methylpropylamino, methylbenzylamino, methyl-p-chlorophenylamino, methylcyclohexylamino, methylphenylamino, methyltoluylamino, and so forth. Exemplary tertiary amines include N,N-diethylaniline, N,N-dimethylglycine, triethanolamine, triethylamine, and trimethylamine.

Amides

Amides, as will be appreciated by those skilled in the art, have the molecular structure R$^4$—(CO)—NR$^5$R$^6$ where R$^4$, R$^5$ and R$^6$ are generally selected from H, alkyl, cycloalkyl, cycloalkyl-substituted alkyl, monocyclic aryl, and monocyclic aryl-substituted alkyl. Examples of suitable amides herein include, without limitation, hexamethyleneacetamide, hexamethyleneoctamide, hexamethylene lauramide, hexamethylene palmitamide, N,N-dimethyl formamide, N,N-dimethyl acetamide, N,N- dimethyloctamide, N,N-dimethyldecamide, toluamide, dimethyl-m-toluamide, diethyl-m-toluamide, and combinations thereof.

Nitrogen-containing Heterocycles

Nitrogen-containing heterocycles suitable as the pharmacologically active base herein include, by way of example, 2-pyrrolidone, 1-methyl-2-pyrrolidone, 5-methyl-2-pyrrolidone, 1,5-dimethyl-2-pyrrolidone, 1-ethyl-2-pyrrolidone, 1-propyl-3-dodecylpyrrolidine, 1-dodecyclazacycloheptan-2-one, ethylene thiourea, hydantoin, oxalylurea, imidazolidilyl urea, N-octadecyl morpholine, dodecylpyridinium, N-dodecylpyrrolidine, N-dodecylpiperidine, N-dodecylhomopiperidine, and combinations thereof.

Aromatic nitrogen-containing heterocycles, typically contain a 5- or 6-membered monocyclic substituent, or a bicyclic fused or linked 5- or 6-membered ring, such as imidazolyl, indolyl, pyridinyl, pyrimidinyl, pyrrolyl, quinolinyl, tetrazolyl, 1,2,4-triazolyl, etc.

Aromatic nitrogen-containing heterocycles suitable as the organic base herein include, by way of example, 2-aminopyridine, benzimidazole, 2,5-diaminopyridine, 2,4-dimethylimidazole, 2,3-dimethylpyridine, 2,4-dimethylpyridine, 3,5-dimethylpyridine, imidazole, methoxypyridine, γ-picoline, 2,4,6-trimethylpyridine, and combinations thereof.

Non-aromatic nitrogen-containing heterocycles, typically contain 4- to 6-membered rings such as acetimido, morpholinyl, lactams and imides (e.g., -butyrolactam, -caprolactam, N-phenyl—propiolactam), phthalimido, piperidyl, piperidino, piperazinyl, pyrrolidinyl, succinimido, etc.

Non-aromatic nitrogen-containing heterocycles include, by way of example, 1,2-dimethylpiperidine, 2,5-dimethylpiperazine, 1,2-dimethylpyrrolidine, 1-ethylpiperidine, n-methylpyrrolidine, morpholine, piperazine, piperidine, pyrrolidine, 2,2,6,6-tetramethylpiperidine, 2,2,4-trimethylpiperidine, and combinations thereof.

For all pharmacologically active bases herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation is effective to provide a pH at the skin surface, upon application of the formulation, in the range of about 7.5 to about 13.0, preferably about 8.0 to about 11.5, and most preferably in the range of about 8.5 to about 10.5. This in turn ensures that the degree of treatment is maximized while the possibility of damage to the body surface is eliminated or at least substantially minimized.

IV. Pharmaceutical Formulations and Skin Patches

The pharmaceutical formulation of the invention comprises a pharmaceutically acceptable topical carrier, a base (which serves as an antifungal agent), and, preferably, an additional pharmacologically active antifungal compound (in which case the base also serves as a permeation enhancer for the compound). The base is present at a concentration sufficient to provide a formulation pH in the range of approximately 7.5 to 13.0, preferably about 8.0 to 11.5, and most preferably about 8.5 to 10.5.

Pharmacologically active antifungal agents include, without limitation: amorolfine; ciclopirox olamine; flucytosine; griseofulvin; haloprogrin; potassium iodide sodium pyrithione; undecylenic acid; imidazole derivatives, including without limitation bifonazole, butoconazole, clotrimazole, econazole, ketoconazole, miconazole, oxiconazole, and sulconazole; triazoles, including without limitation itraconazole, fluconazole, and terconazole; allylamines, including without limitation naftifine and terbinafine; polyene antifungal antibiotics such as amphotericin B and nystatin; antifungal organic acids such as benzoic acid, salicylic acid, propionic acid, and caprylic acid; and a propylene glycol-urea-lactic acid combination. One or more additional active antifungal agents may optionally be present in the formulation. The choice of a particular pharmacologically active fungal agent will be readily apparent to those skilled in the art. For example, an onychomycotic infection caused by a dermatophyte may be treated by an antifungal agent effective against dermatophytes, such as terbinafine. As another example, a case of onychomycosis of uncertain fungal etiology may be treated with a broad-spectrum antifungal agent effective against dermatophytes, nondermatophyte molds, and yeasts, such as itraconazole. Preferred antifungal agents include amorolfine, ciclopirox olamine, terbinafine, itraconazole, fluconazole, clotrimazole, and nystatin.

The formulation may be in any form suitable for application to the nail and surrounding tissues, and may comprise, for example, a cream, lotion, solution, gel, ointment, paste, plaster, paint, bioadhesive, or the like, and/or may be prepared so as to contain liposomes, micelles, and/or microspheres. For those formulations in which the pharmacologically active base is a hydroxide-releasing agent, it is preferred although not essential that water be present. Thus, such a formulation may be aqueous, i.e., contain water, or may be nonaqueous and optionally used in combination with an occlusive overlayer so that moisture evaporating from the body surface is maintained within the formulation upon application to the body surface and thereafter.

Formulations of the invention may optionally contain a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer.

A film former, when it dries, forms a protective film over the site of application. The film inhibits removal of the active ingredient and keeps it in contact with the site being treated. An example of a film former that is suitable for use in this invention is Flexible Collodion, USP. As described in *Remington: The Science and Practice of Pharmacy*, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Creams, as also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Plasters are comprised of a pasty mixture that is spread on the body, either directly or after being saturated into a base material such as cloth. Medications, including the bases of the invention, may be dissolved or dispersed within the plaster to make a medicated plaster.

Bioadhesives are preparations that adhere to surfaces of body tissues. Polymeric bioadhesive formulations are well known in the art; see, for example, Heller et al., "Biodegradable polymers as drug delivery systems", in Chasin, M. and Langer, R., eds.: Dekker, New York, pp.121–161 (1990); and U.S. Pat. No. 6,201,065. Suitable non-polymeric bioadhesives are also known in the art, including certain fatty acid esters (U.S. Pat. No. 6,228,383).

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1–2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the nail and surrounding tissues.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

Although the bases herein are particularly effective permeation enhancers, it may be desirable, particularly with weaker bases or thicker nails, to include an added permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred.

Most preferred enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter of plasticizing enhancers is in the range of about 2.5 to about 10, preferably in the range of about 5 to about 10. Such enhancers are described in detail in co-pending, commonly assigned U.S. patent application Ser. No. 09/738,410, filed on Dec. 14, 2000, which is now U.S. Pat. No. 6,586,000, and in International Patent Application No. PCT/US00/34483, filed on Dec. 15, 2000, published Jun. 21, 2001 as WO 01/43775 A2. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$–$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., *Percutaneous Penetration Enhancers*, Smith et al., editors (CRC Press, 1995).

Various additives, known to those skilled in the art, may be included in the topical formulations. For example, solvents, including relatively small amounts of alcohol, may be used to solubilize certain formulation components. The present formulations may also include conventional additives such as opacifiers, antioxidants, fragrance, colorants, gelling agents, thickening agents, stabilizers, surfactants, and the like. Other agents may also be added, such as antimicrobial agents, to prevent spoilage upon storage, i.e., to inhibit growth of microbes such as bacteria, yeasts, and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The formulations may also contain irritation-mitigating additives to minimize or eliminate the possibility of skin irritation or skin damage resulting from the base or other components of the composition. Suitable irritation-mitigating additives include, for example: -tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the composition.

The base may also be administered through the nail and surrounding tissues using a conventional skin patch, wherein the agent is contained within a laminated structure that serves as a drug delivery device to be affixed to the body surface. In such a structure, the pharmaceutical formulation is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the nail or skin during drug delivery; typically, the adhesive material is a pressure-sensitive adhesive (PSA) that is suitable for long-term skin or nail contact, and that should be physically and chemically compatible with the base and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, base, or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and nail and be worn comfortably on areas of skin such as at joints or other points of flexure, that are normally subjected to mechanical strain, with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the nail and/or skin surrounding the nail. The release liner should be made from a drug/vehicle impermeable material, and is a disposable element that serves only to protect the device prior to application. Typically, the release liner is formed from a material impermeable to the pharmacologically active agent and the base, and which is easily stripped from the patch prior to use.

In an alternative embodiment, the active agent-containing reservoir and skin or nail contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be an active agent, an enhancer, or some other component contained in the drug delivery system. A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the nail and skin contact area, has an area in the range of about 0.25 cm$^2$ to 12 cm$^2$, preferably about 0.5 cm$^2$ to 7 cm$^2$, more preferably about 1 cm$^2$ to 5 cm$^2$. That area will vary, of course, with the size of the area to be treated. Larger patches will be necessary to accommodate larger nails, whereas smaller patches can be used for smaller nails.

Such drug delivery systems may be fabricated using conventional coating and laminating techniques known in the art. For example, adhesive matrix systems can be prepared by casting a fluid admixture of adhesive, active agent and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, these patches are fabricated by solvent evaporation, film casting, melt extrusion, thin film lamination, die cutting, or the like. The active agent will generally be incorporated into the device during patch manufacture rather than subsequent to preparation of the device.

In a preferred delivery system, an adhesive overlayer that also serves as a backing for the delivery system is used to better secure the patch to the nail and surrounding tissue. This overlayer is sized such that it extends beyond the drug reservoir so that adhesive on the overlayer comes into contact with the body surface. In many cases, the overlayer will make contact with the skin surrounding the nail, while the drug reservoir is positioned over the nail, particularly the infected portions of the nail. The overlayer is useful because the adhesive/drug reservoir layer may lose its adhesion a few hours after application due to hydration. By incorporating such adhesive overlayer, the delivery system remains in place for the required period of time.

Other types and configurations of topically applied drug delivery systems may also be used in conjunction with the present invention, as will be appreciated by those skilled in the art of topical drug delivery. See, for example, Ghosh, *Transdermal and Topical Drug Delivery Systems* (Interpharm Press, 1997), particularly Chapters 2 and 8.

V. Administration

The method of delivery may vary, but necessarily involves application of a formulation of the invention to an area of body surface affected with onychomycosis. A cream, ointment, paste, plaster, or lotion may be spread on the affected area and gently rubbed in. Similarly, a polymeric or other bioadhesive formulation may be spread or dabbed on the affected area. A solution may be applied in the same ways, but more typically will be applied with a dropper, swab, or the like, and carefully applied to the affected area. Petrolatum may be spread on the skin surrounding the affected area to protect it from possible irritation during treatment.

The dose regimen will depend on a number of factors that may readily be determined, such as the areal extent and thickness of the affected nail and the responsiveness of the infection to treatment, but will normally be one or more doses per day, with a course of treatment lasting from several weeks to several months, or until a cure is effected or a significant reduction of the infection is achieved. One of ordinary skill may readily determine optimum dosages, dosing methodologies and repetition rates. In general, it is contemplated that the formulation will be applied one to four times daily. With a skin patch, the device is generally maintained in place on the body surface throughout a drug delivery period, typically in the range of 8 to 72 hours, and replaced as necessary.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains. Furthermore, the practice of the present invention will employ, unless otherwise indicated, conventional techniques of drug formulation, particularly topical and transdermal drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

All patents, patent applications, and publications mentioned herein are hereby incorporated by reference in their entireties.

Experimental

The practice of the present invention will employ, unless otherwise indicated, conventional techniques of pharmaceutical formulation and the like, which are within the skill of the art. Such techniques are fully explained in the literature. In the following examples, efforts have been made to ensure accuracy with respect to numbers used (e.g., amounts, temperatures, etc.) but some experimental error and deviation should be accounted for. Unless otherwise indicated, temperature is in degrees Celsius and pressure is at or near atmospheric pressure at sea level. All reagents were obtained commercially unless otherwise indicated.

EXAMPLE 1

A topical gel of the invention is prepared by conventional pharmaceutical methods. The indicated amounts of the following ingredients are used:

| Ingredient | Amount |
| --- | --- |
| Purified water | 600 grams |
| Polyethylene glycol | 400 grams |
| Potassium hydroxide | 0.01 gram |
| Edetate disodium | 0.1 gram |
| Carbomer 934P | 12.5 grams |
| Poloxamer 407 | 2.0 grams |
| Polysorbate 40 | 2.0 grams |
| Butylated hydroxytoluene | 0.5 grams |
| Benzyl alcohol | 10.0 grams |

The carbomer 934P and the edetate disodium are added to 250 mL of the purified water, and the mixture is homogenized at low speed until the carbomer is dispersed. Next, the polaxamer 407, mixed with 250 mL of the purified water, is added to the carbomer mixture, and the resulting mixture is homogenized at low speed. The potassium hydroxide, dissolved in 100 mL of purified water, is added to this mixture, and the resulting mixture (Mixture 1) is homogenized at low speed. In a separate container, the polysorbate 40 and the butylated hydroxytoluene are added to the polyethylene glycol, and the resulting mixture is heated to 65° C. and maintained at this temperature until all the compounds are dissolved; this mixture is then allowed to cool to room temperature, at which time the benzyl alcohol is added, and the resulting mixture is homogenized at low speed. This mixture is then added to Mixture 1, and the resulting mixture is mixed at low speed until it is homogeneous, forming a gel of the invention.

EXAMPLE 2

A topical cream of the invention is prepared by conventional pharmaceutical methods. The indicated amounts of the following ingredients are used:

| Ingredient | Amount |
| --- | --- |
| Purified water | 370 grams |
| White petrolatum | 250 grams |
| Stearyl alcohol | 250 grams |
| Propylene glycol | 120 grams |
| Sodium lauryl sulfate | 10 grams |
| Methylparaben | 0.25 gram |
| Propylparaben | 0.15 gram |
| Potassium hydroxide | 0.01 gram |

The stearyl alcohol and the white petrolatum are melted together on a steam bath, and then maintained at a temperature of approximately 75° C. The other ingredients are then added, after previously having been dissolved in the purified water and warmed to 75° C., and the resulting mixture is stirred until it congeals into a cream of the invention.

EXAMPLE 3

A skin patch of the invention is prepared by conventional pharmaceutical methods. A square piece of sterile, finely woven gauze one centimeter on each side is placed in the center of a square piece of occlusive surgical adhesive tape two centimeters on each side. To the gauze is applied 0.4 mL of the gel of Example 1; the gel is allowed to soak into the gauze. This skin patch of the invention is used within three hours of preparation.

EXAMPLE 4

The gel formulation of Example 1 is provided to patients having distal subungual onychomycosis. Each infected nail to be treated is examined, cultured, and photographed before treatment begins. Culturing is performed as described by B. Elewski (Journal of the American Academy of Dermatology, v. 35 (number 3, part 2): S6–S9): The nail to be sampled is first swabbed liberally with alcohol to eliminate as many bacteria as possible, as bacteria could overgrow and inhibit the growth of fungi. A small curette or special nail clipper is used to cut away the distal end of the nail plate; a curette is then used to scrape debris from the nail bed at a site as close to the cuticle as possible; scrapings from the under surface of the nail plate may be included. The shavings specimen is divided in half, each half being spread on a petri dish containing Sabouraud glucose agar. One petri dish is cycloheximide-free, while the other contains cycloheximide in the agar. Chloramphenicol is usually added to the culture media in both dishes to inhibit bacterial growth. The dishes are incubated for 7 to 14 days and then examined microscopically to identify any fungal or yeast growth. As cycloheximide inhibits nondermatophyte growth but not dermatophyte growth, colonies that appear on both dishes are likely to be dermatophytes, while those that only appear on the cycloheximide-free dish are likely to be nondermatophyte species.

Each of the patients is instructed to topically apply the formulation of the invention to the affected nail or nails twice daily for eight weeks. The patients return to the clinic every seven days, when each nail is again examined, cultured, and photographed. It is found that most of the infected nails are significantly improved in clinical appearance and that the degree of mycological infection as revealed by culturing is significantly reduced after three weeks and that most infections have entirely resolved after eight weeks of treatment.

EXAMPLE 5

The skin patches of Example 3 are provided to patients having onychomycosis on one or more fingernails. Each infected nail to be treated is examined, cultured, and photographed before treatment begins. Culturing is performed as in Example 4. Each of the patients is instructed to topically apply a skin patch of the invention to the affected nail or nails, replacing the old patch with a new one every 48 hours. The patients return to the clinic every seven days, when each nail is again examined, cultured, and photographed. It is found that most of the infected nails are significantly improved in clinical appearance and that the degree of mycological infection as revealed by culturing is significantly reduced after three weeks and that most infections have entirely resolved after eight weeks of treatment.

EXAMPLE 6

The cream formulation of Example 2 is provided to patients having white superficial onychomycosis. Each infected nail to be treated is examined, cultured, and photographed before treatment begins. Culturing is performed as in Example 4, except that the specimen is obtained by scraping debris from the surface of the infected nail with a No. 15 blade scalpel or a sharp curette. Each of the patients is instructed to topically apply the formulation of the invention to the affected nail or nails twice daily for eight weeks. The patients return to the clinic every seven days, when each nail is again examined, cultured, and photographed. It is found that most of the infected nails are significantly improved in clinical appearance and that the degree of mycological infection as revealed by culturing is significantly reduced after three weeks and that most infections have entirely resolved after eight weeks of treatment.

We claim:

1. A method of treating an individual afflicted with onychomycosis, comprising topically applying to an affected area of the individual's nail and surrounding tissue a formulation consisting essentially of a pharmaceutically acceptable topical carrier, an effective skin-permeation enhancing amount of an inorganic hydroxide or a mixture thereof, and a therapeutically effective amount of an antifungal agent, wherein the effective skin-permeation enhancing amount corresponds to a concentration sufficient to provide a formulation pH in the range of approximately 7.5 to 13.0, wherein the formulation does not contain any additional permeation enhancers.

2. The method of claim 1, wherein the antifungal agent is selected from the group consisting of terbinatine, amorolfine, ciclopirox olamine, flucytosine, griseofulvin, haloprogrin, potassium iodide, sodium pyrithione, undecylenic acid, imidazoles, triazoles, allylamines, polyene antifungal antibiotics, antifungal organic acids, and a propylene glycol-urea-lactic acid combination.

3. The method of claim 2, wherein the antifungal agent is selected from the group consisting of amorolfine, ciclopirox olamine, flucytosine, griseofulvin, haloprogrin, potassium iodide, sodium pyrithione, undecylenic acid, bifonazole, butoconazole, clotrimazole, econazole, ketoconazole, miconazole, oxiconazole, sulconazole, itraconazole, fluconazole, terconazole, naftifine, amphotericin B, nystatin, benzoic acid, salicylic acid, propionic acid, and caprylic acid.

4. The method of claim 2, wherein the pharmacologically active antifungal agent is ciclopirox olamine.

5. The method of claim 2, wherein the pharmacologically active antifungal agent is terbinafine.

6. The method of claim 2, wherein the pharmacologically active antifungal agent is itraconazole.

7. The method of claim 2, wherein the pharmacologically active antifungal agent is fluconazole.

8. The method of claim 2, wherein the pharmacologically active antifungal agent is clotrimazole.

9. The method of claim 2, wherein the pharmacologically active antifungal agent is nystatin.

10. The method of claim 1, wherein the pH is in the range of approximately 8.0 to 11.5.

11. The method of claim 1, wherein the pH is in the range of approximately 8.5 to 10.5.

12. The method of claim 1, wherein the formulation is aqueous.

13. The method of claim 12, wherein the aqueous formulation is selected from the group consisting of a cream, a gel, a lotion, a paste, and a solution.

14. The method of claim 13, wherein the aqueous formulation is a cream.

15. The method of claim 13, wherein the aqueous formulation is a gel.

16. The method of claim 13, wherein the aqueous formulation is a lotion.

17. The method of claim 13, wherein the aqueous formulation is a solution.

18. The method of claim 13, wherein the aqueous formulation is a paste.

19. The method of claim 1, wherein the formulation is a bioadhesive.

20. The method of claim 1, wherein the formulation is in a medicated plaster.

21. The method of claim 1, wherein the formulation is in a skin patch.

22. The method of claim 1, wherein the inorganic hydroxide is selected from the group consisting of ammonium hydroxide, alkali metal hydroxides, alkaline earth metal hydroxides, and mixtures thereof.

23. The method of claim 22, wherein the inorganic hydroxide is selected from the group consisting of ammonium hydroxide, sodium hydroxide, calcium hydroxide, potassium hydroxide, magnesium hydroxide, and mixtures thereof.

24. The method of claim 23, wherein the inorganic hydroxide is sodium hydroxide.

25. The method of claim 1, wherein the formulation contains an additional active antifungal agent.

26. The method of claim 1, wherein the formulation is applied periodically over an extended time period.

27. The method of claim 1, wherein the formulation is applied approximately twice weekly.

28. The method of claim 1, wherein the formulation is applied once daily.

29. The method of claim 1, wherein the formulation is applied twice daily.

30. The method of claim 1, wherein the formulation is applied on an as-needed basis.

31. The method of claim 26, wherein said extended time period is at least three months.

32. The method of claim 31, wherein said extended time period is at least four months.

* * * * *